(12) United States Patent
Blizard et al.

(10) Patent No.: US 7,968,840 B2
(45) Date of Patent: Jun. 28, 2011

(54) OPTICAL PHASE REFERENCE

(75) Inventors: Benjamin Blizard, Mountain View, CA (US); Charles Kamas, San Jose, CA (US); Edward Pruitt, Simi Valley, CA (US)

(73) Assignee: Finesse Solutions, LLC, San Jose, CA (US)

( * ) Notice: Subject to any disclaimer, the term of this patent is extended or adjusted under 35 U.S.C. 154(b) by 3 days.

(21) Appl. No.: 12/290,206

(22) Filed: Oct. 28, 2008

(65) Prior Publication Data

US 2010/0102214 A1    Apr. 29, 2010

(51) Int. Cl.
*G01D 18/00*    (2006.01)
(52) U.S. Cl. .................................................. 250/252.1
(58) Field of Classification Search ............... 250/252.1, 250/459.1
See application file for complete search history.

(56) References Cited

U.S. PATENT DOCUMENTS

| | | | | |
|---|---|---|---|---|
| 4,374,328 A * | 2/1983 | Tekippe et al. | ............. | 250/458.1 |
| 4,895,156 A * | 1/1990 | Schulze | ......................... | 600/342 |
| 5,381,666 A * | 1/1995 | Saho et al. | ..................... | 62/47.1 |
| 6,426,505 B1 * | 7/2002 | Rao et al. | ..................... | 250/458.1 |
| 2002/0190221 A1 * | 12/2002 | Hutchison | ................. | 250/459.1 |
| 2007/0057198 A1 * | 3/2007 | Wilson et al. | ............. | 250/458.1 |
| 2008/0130695 A1 * | 6/2008 | Riddle et al. | .................... | 372/33 |

* cited by examiner

*Primary Examiner* — David P. Porta
*Assistant Examiner* — Kiho Kim
(74) *Attorney, Agent, or Firm* — Herbert Burkard

(57) ABSTRACT

A validation apparatus for testing the measurement accuracy of a phase fluorimeter comprising:
i) a photodetector responsive to the excitation light emitted by a phase fluorimeter;
ii) electronics connected to the detector which calculates the phase of the light emitted by the phase fluorimeter and causes a light source in the validation apparatus to emit light of a wave length which will stimulate the detector of the phase fluorimeter but which is phase shifted relative to the light emitted by the phase fluorimeter.

10 Claims, 8 Drawing Sheets

D

C

OPTICAL PHASE REFERENCE

FIELD OF THE INVENTION

This invention pertains to the testing (validation) of phase-fluorimetric based sensors. For example, the invention allows the user to confirm that the phase sensitive fluorescent detection based system in question is correctly functioning. This allows these sensors to be used in any application where proof of correct measurements is required. For example, confirmation of correct function is required to comply with legal standards for the production of pharmaceuticals. These standards are often referred to as current good manufacturing practices, or cGMPs. In the United States and the EU, these standards are set in section 21 of the Code of Federal Regulations, part 211 and 210; and EEC Directive 2003/94/EC, respectively. Compliance with these standards are required for access to these markets, and demonstrated compliance is required in order to manufacture a drug for human consumption.

BACKGROUND OF THE INVENTION

The creation and mass production of biotech based drugs represents a large endeavor and a significant segment of our economy. Many older methods of synthesising drugs are still in use while new techniques are constantly being developed. In particular, the subset of drugs that are biologically derived is rapidly growing. These biologically derived drugs are typically manufactured by growing cells that have been genetically engineered to produce a protein or other molecule of interest. These cells generally require an environment in which all or at least most of the temperature, pH, dissolved oxygen, dissolved $CO_2$, glucose, lactate, and amino acid levels are monitored and/or controlled. A bioreactor is a vessel that is often used to provide such a controlled growth environment. These vessels have evolved over many years and have been designed and tested to ensure that they can provide the conditions required. However, irrespective of whether or not the bioreactor vessel itself can meet the requirements, control systems and sensors are always needed and must be monitored appropriately in order to consistently and reproducibly provide the desired conditions. Additionally, it is often necessary to document this reproducibility in order to meet the standards set forth by the pharmaceutical industry or the United States Food and Drug Administration (FDA). In order to meet the requirements of the industry with regard to reproducibility, sterility, robustness, and reliability new technologies are being developed that more accurately and economically allow a drug manufacturer to monitor and control the cell's environmental parameters. The end goal is to manufacture the desired end-product more reliably and at reduced cost.

As mentioned, the pharmaceutical industry must conform to many of the FDA's requirements which are intended to guarantee safe and effective drugs. Compliance with FDA requirements not only determines many of the processes that are put in place when manufacturing pharmaceutical and biotech products, but also drives many cost models for drug companies. One area that exemplifies the impact of FDA regulations on manufacturing methods and costs is specifically those regulations that pertain to the electronic equipment used in the manufacture of pharmaceuticals.

Specifically, The FDA enforces 21 CFR Parts 210 and 211 at all pharmaceutical production sites. Specifically, this requires that automated testing equipment systems perform satisfactorily and be checked for correct calibration on a regular basis (see e.g., 21 CFR section 211.68). Similar requirements often apply outside the United States. For example, in the EEC, Other requirements such as Commission Directives 91/356/EEX, 2003/94/EC, and 91/412/EEC may be applicable.

Phase fluorimetry is a technique that can be used to provide sensor instruments ("phase fluorimeters") able to monitor many of the critical parameters in a bioreactor. Phase fluorimetry typically utilizes a fluorescent material (also referred to as a fluorescent dye or fluorophore) which has an upper-state lifetime that is quenched by the presence of a target analyte. Herein a fluorescent material is defined as a material which emits light at a lower frequency after illumination (stimulation) by an optical source. When sinusoidally modulated light is used to illuminate the fluorescent material, the emitted light is smaller in amplitude but is also sinusoidally modulated and delayed in phase with respect to the illumination light. This relationship between the illumination light and emitted light is shown in FIG. 1. In this Figure, 1 is the excitation source sine wave and 2 is the emitted or fluorescent signal's sine wave.

The difference in phase, $\Phi$, between the excitation and emission light is proportional to the concentration of the quenching analyte and can therefore be used as an indicator of the concentration of that analyte. This difference is referred to variously as a delay or a shift. The terms are interchangeable in this situation. The fluorescent material, or fluorophore, must be selected or developed to be quenched by the particular analyte under study. This quenching is commonly modeled using the Stem-Volmer equation:

$$\frac{F_0}{F} = \frac{\gamma + k_q[Q]}{\gamma} \quad \text{(Equation 1)}$$

This quantifies the fractional change in fluorescence when quenching is increased. In this equation, $\gamma$ is the decay rate of the fluorescence without additional quenching, $k_q$ is the bimolecular quenching constant, which measures the likelihood and effectiveness of quenching events, and $[Q]$ is the concentration of the fluorophore. Both $\gamma$ and $k_q$ are functions of temperature. This equation can be re-written to give the change in the decay time of the fluorophore as a function of quencher concentration. When this is done, the Stem-Volmer equation becomes $$\frac{\tau}{\tau_0} = \frac{\gamma}{\gamma + k_q[Q]} = \frac{1}{1 + \tau_0 k_q[Q]} \quad \text{(Equation 2)}$$

Note that the decay rate is defined as the inverse of the characteristic decay time, $\tau_0$. I.e., $\gamma^{-1}\tau_0$ (Lackowicz, *Principles of Fluorescence Spectroscopy*, $3^{rd}$ edition, Springer 2006).

A typical set of data from a phase fluorimeter and an oxygen-quenched fluorescent dye is shown in FIG. 2. These curves are generated by utilizing a phase fluorimeter to measure known concentrations of the analyte at different temperatures. The sensitivity of the phase response to temperature in the range from 5° C. to 45° C. in steps of 10° C. is apparent in FIG. 2. This temperature range covers the operating temperature of the majority of bioprocesses.

Once these curves are measured they can be used to find functional forms (using algebraic or numerical fits) for $k_q$ and $\tau_0$ as functions of temperature or other relevant parameter and thus calibrate the sensor. Once the calibration is known, the oxygen concentration can be measured using an instrument that incorporates a phase fluorimeter and has had the fluorophore and instrument characterized by production of such curves. Without calibration, minor variations in any of the relevant parameters can cause a difference in phase that will give an erroneous reading.

The Stern-Volmer equation is one of the simplest equations describing the variation of fluorescence as a function of environmental parameters (γ, temperature, quencher concentration). More complicated equations exist and are used as the basis for phase fluorimeters. Calibration is done in a similar manner—the parameters that can impact phase in the specific situation where the phase fluorimeter is used are measured and their impact is corrected.

However, a problem arises because it is not uncommon for the properties of any fluorophore to change after a period of use. The analyte sensitive fluorescent dye's properties will frequently change as a result of long term exposure to both the analyte under study as well as to ambient light. This change in properties usually results in a change in the phase delay vs. concentration curve which means that the original calibration data is no longer valid and the readings are to a greater or lesser extent incorrect. Additionally, if the phase fluorimeter itself exhibits drift or is otherwise not capable of accurately and precisely reading the phase delay the result is a limit to the accuracy and precision of the sensor. As discussed above, in the pharmaceutical and biotech manufacturing sector, sensor performance is regulated by the Federal Code of Regulations and specifically, 21 CFR Part 11. The performance of a device used in the manufacturing of drugs is required to be tested for accuracy and function (e.g.: validated) on a regular and periodic basis in order to ensure that the drug efficacy and quality has not changed.

DESCRIPTION OF THE INVENTION

Currently no apparatus is commercially available to systematically validate the performance of sensor instruments (i.e., phase fluorimeters) that utilize phase fluorimetry for analyte detection. The purpose of the present invention is to allow the user of such sensors to test the performance, accuracy, and precision of their device as is required for use, for example, in a cGMP environment. While the invention description has centered on use in the biopharmaceutical manufacturing arena, this invention and the general concepts discussed herein can be applied anywhere that phase fluorimetry is used for analyte detection.

Figure 1:
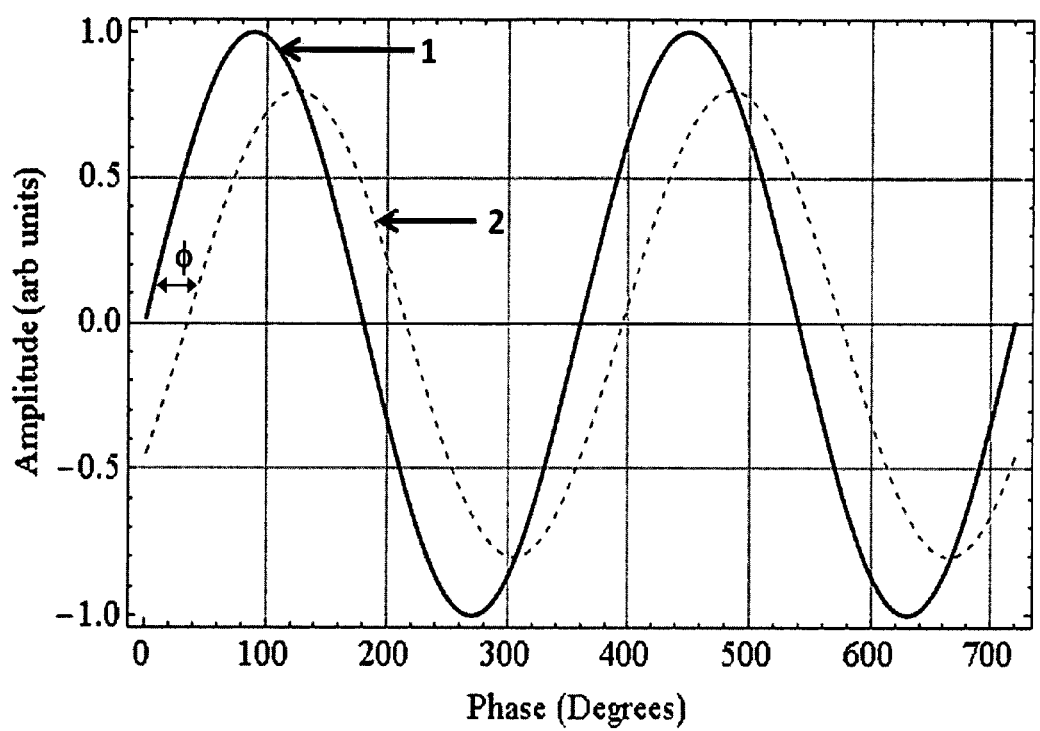
FIG. 1 is a graph showing the relationship between the light used to excite the fluorophore and the light emitted by a typical fluorophore.
Figure 2:
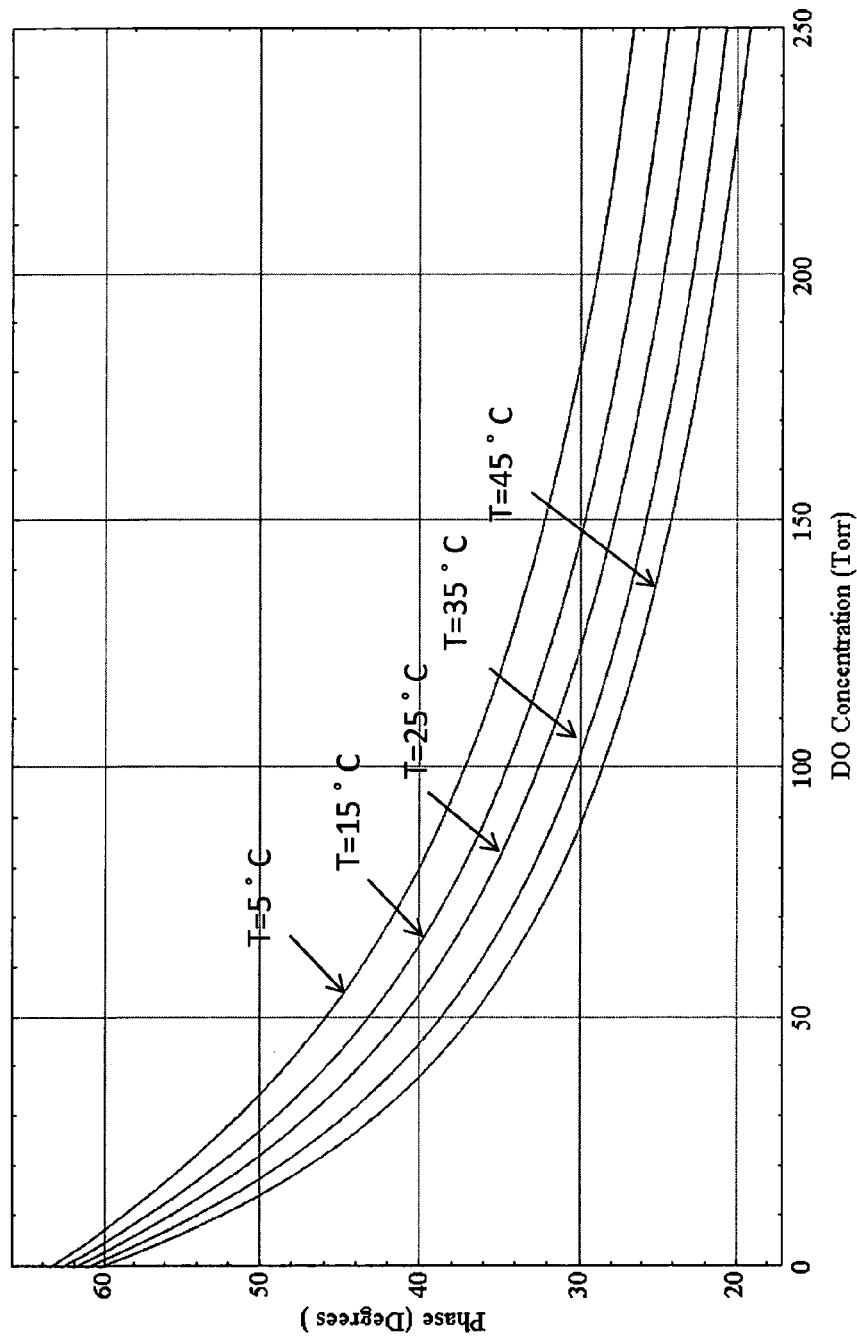
FIG. 2 is a graph plotting a typical set of data from a phase fluorimeter. The curves are generated by utilizing a phase fluorimeter to measure known concentrations of an analyte (Oxygen in this case) at different temperatures.
Figure 3:
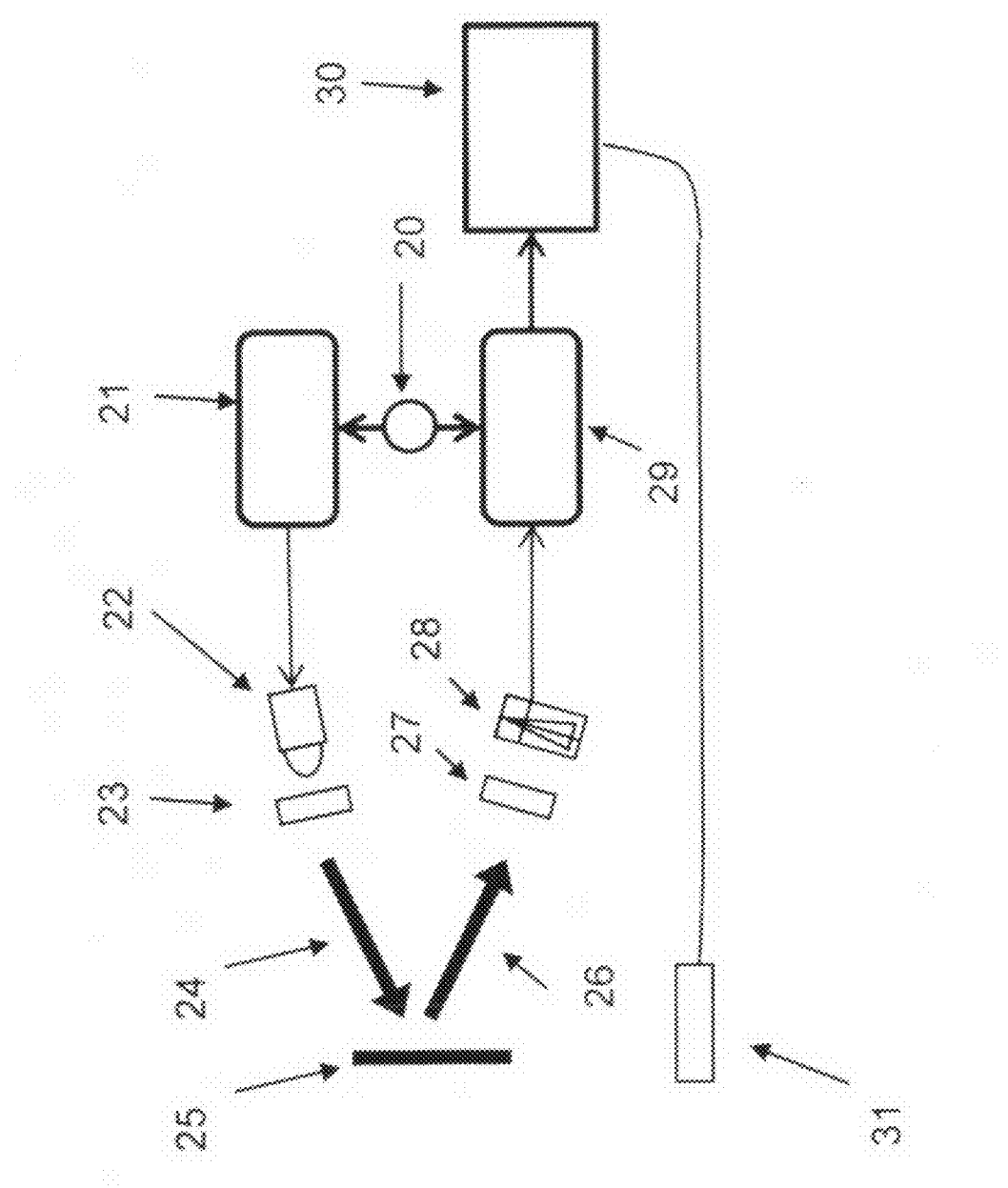
FIG. 3 is a schematic of a phase fluorimetry based sensor.

To more readily understand the operation of the present invention it is helpful to review in more detail how phase fluorimeters work in order to thereby more readily understand how the present invention is used to verify that they are working correctly and providing an accurate result. A phase fluorometric system can be divided into three main components: the fluorescent sensor dye (equivalently called a fluorophore), the optical illumination and detection system, and the electronics that drive the optical source and calculate the phase delay of the fluorescent signal. A schematic of a sensor based on phase fluorimetry is shown in FIG. 3. In this figure, 20 is the sine wave generator which can be used in both the excitation wave generation process and optionally in the phase measurement process, 21 denotes the drive electronics, 22 is the excitation light source (e.g., a LED, laser diode, etc), 23 is an optical filter which only passes light 24 that matches the absorption spectrum of the sensor dye 25. The fluorescent signal 26 impinges on a filter 27 which prevents other light sources from impinging on the optical detector 28. The resulting electronic signal is compared to the excitation wave's phase by analog or digital means using electronics shown as 29. The resulting phase number is displayed on display 30 along with the temperature taken using instrument 31 which can be an resistive temperature detector (RTD), thermistor, or equivalent temperature measuring apparatus.

Figure 4:
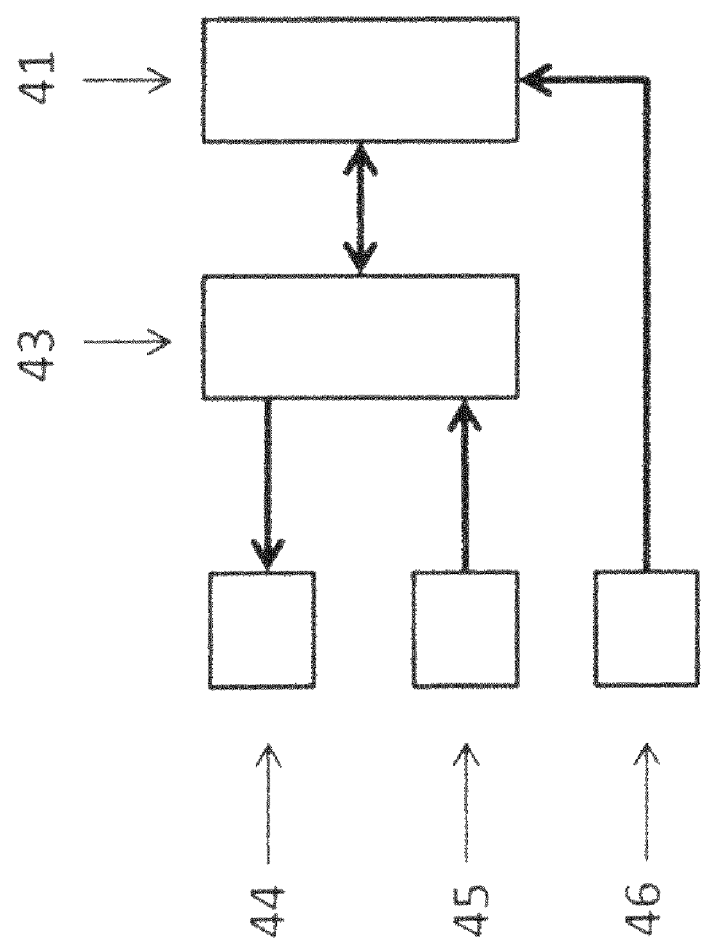
FIG. 4 is a block diagram showing the fluorimetric measurement process.

In FIG. 4, a block diagram of the process is shown where 41 is the central electronic processing unit which can generate the sine waves and display the results as well as convert the units of the temperature transducer to a displayed temperature value. The sine wave signal is sent to the drive and amplification electronics 43. The excitation light is created by a suitable optical device 44, and the fluorescent signal is received by the detection system 45, which sends the signal back to the electronics system 43 to amplify and reduces the information to a phase delay relative to the excitation source. The temperature sensor 46 sends a signal to electronics 43. It should be noted here that the different electronic functions can be consolidated or configured separately without affecting the system's ability to create the same results.

Figure 5:
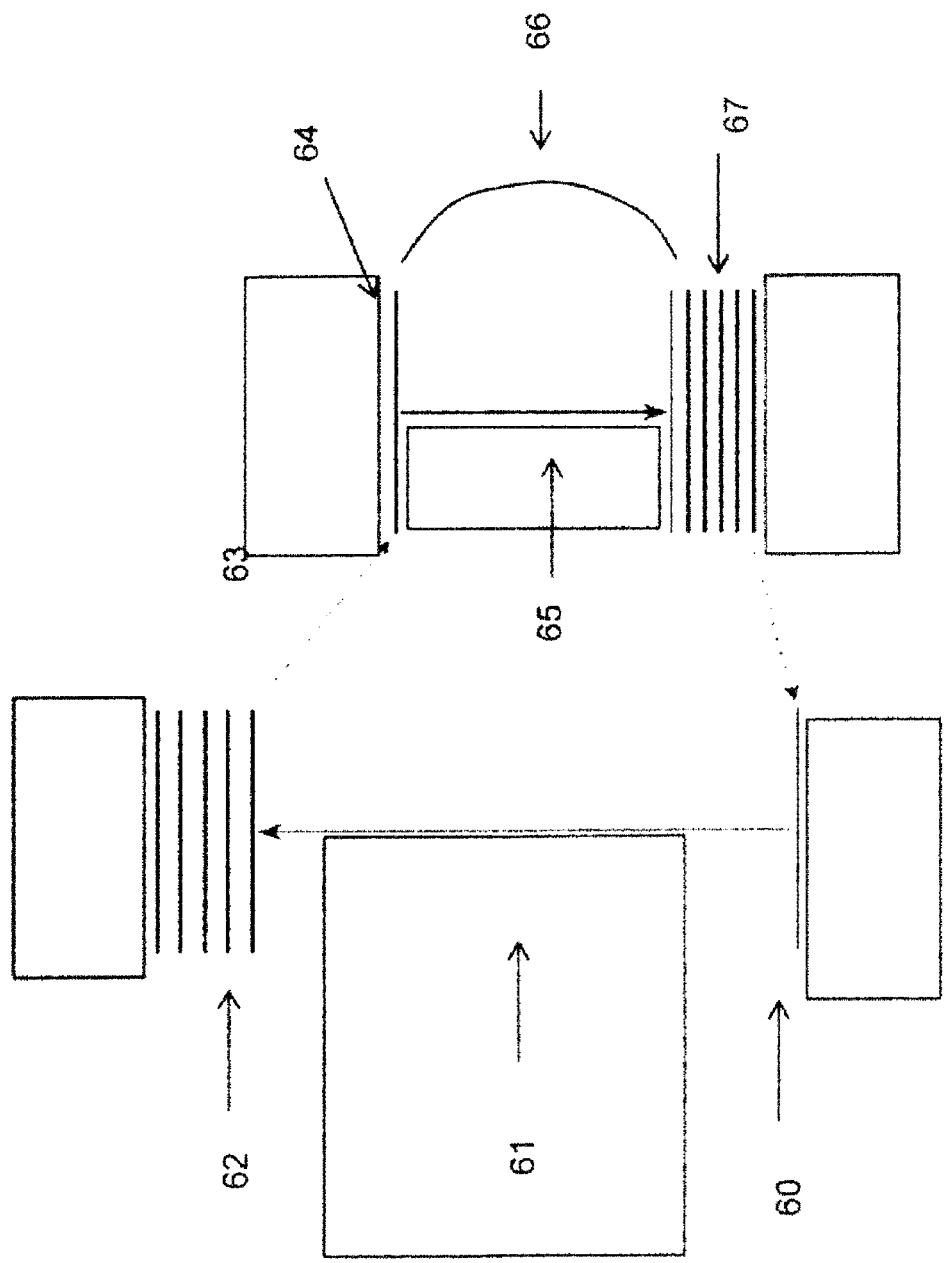
FIG. 5 is a schematic illustration of the quenching process whereby collisions between the analyte and the excited fluorophore electrons allows a non-optical pathway for the relaxation of the excited state back down to a lower energy state.

The fluorophore shown as 25 in FIG. 3 absorbs light and re-emits this light at a red-shifted (lower energy) wavelength. The extent to which the re-emitted light is time delayed and its amplitude is reduced is a function of both the particular fluorophore and the concentration of specific analyte being measured. Fluorophores vary widely in their compositions and characteristics, but a general model can be used to represent the process. As the fluorophore is excited by a light source, its electrons are elevated to a higher energy state. In this state, the electrons can relax by shedding some of their energy through the generation of photons, and also through non-radiative relaxation pathways. Light is emitted when a transition between states occurs. The term fluorescent transition usually indicates a spin allowed transition between wave-functions, while the term phosphorescence usually refers to a spin forbidden transition. For the purposes of our invention, the particular type of transition is unimportant. The fundamental aspect is that the emitted light is modulated in response to the modulation of the pump light. The apparent rate at which these transitions occur, or equivalently the time for the upper optical state to decay, is affected by the presence of the analyte under study. Quenching is a process whereby collisions between the analyte and the excited electrons allows a non-optical pathway for the relaxation of the excited state back down to the lower set of vibrational energy states (a "manifold") as shown in FIG. 5. Here 60 is the equilibrium ground state, 61 is the excitation energy, and 62 is the Frank Condon excited state manifold. The excited electron typically relaxes though a phonon mediated process shown here as 63 and arrives at the equilibrium excited state 64. From the excited state there are two relaxation pathways. The first is through fluorescence 65, and the second is through dynamic quenching 66. Dynamic quenching is the fundamental effect in phase fluorimetry (see e.g., Lakowicz, Principles of Fluorescence of Spectroscopy, 3rd edition, Springer 2006). The quenching process brings the electron to 67 which is the Frank Condon ground state manifold. There is then further phonon mediated relaxation back to the equilibrium ground state.

The phase response of the system can be modeled to a first order according to Equation 3 below:

$$\phi = \text{Tan}^{-1}(\omega \tau[\text{concentration}]) \quad \text{(Equation 3)}$$

In Equation 3, $\omega$ is the modulation frequency of the excitation light (and hence the emitted light), $\tau$ [concentration] is the effective fluorescent life time of the sensor dye as a function of the concentration of the analyte, and $\phi$ is the phase of the fluorescent light. As mentioned above, the presence of the analyte being studied quenches the sensor dye and changes the fluorescent lifetime proportionally to the concentration of the analyte present. It should also be noted that as the fluorophores are molecular systems, their energy levels are temperature dependent, as is also the actual dynamic quenching process. In order to accurately characterize the analyte concentration using a phase fluorimetric system, both the phase and the temperature must be accurately known. Depending on the sensor dye used, these requirements can be as stringent as less than 0.1 degree of phase and less than 0.1 deg C.

The optical system of the fluorimeter illuminates the fluorophore with (typically) sinusoidally modulated light and causes the lower energy (longer wavelength) emitted light to impinge on a detector. The optical system can be a fiber optic delivery and collection system or a system using free space optics as shown in FIG. 3. The basic function of the optical system is to illuminate the sensor dye and to collect the emitted signal and optically filter it before it impinges upon the detector. As the excitation light and ambient light have a different phase than the emitted light, the fidelity of the measurement relies on the fact that the optical detector and subsequent electrical signal processing chain sees only the signal of the light emitted by the fluorophore. A well designed fluorimeter will use appropriate optical filtering in front of its optical detector and have the electronics designed so that the level of ingress of signals with other phase components or noise does not affect the fidelity of the measurement.

The result of the entire process is to provide the value of the fluorescent light's phase delay relative to the excitation signal. The electronic system provides the modulated signal which sinusoidally drives the excitation source (e.g., an LED or laser diode). The fluorescent signal impinges upon a photodiode where it is converted to an electronic signal. An electronic system amplifies the detected signal and subsequently processes it. The processing of the signal in order to calculate the phase delay can be either analog or digital, though digital is in general less expensive and more stable. The accuracy and precision of the phase detector are determined by the response of the sensor dye (fluorophore), the modulation frequency of the light source, the signal to noise ratio, and the efficacy of the processing system.

From the above description of how a phase fluorimetric sensor works, it is clear that in order to validate the function of the sensor it is necessary to validate the function of both the electro-optical system and also of the temperature measurement system. This means that an apparatus is required which can generate a signal which is delayed in phase by a known amount from the excitation signal emitted by the fluorimeter. Validation is achieved if the phase delay determined by the phase fluorimeter corresponds to that provided by test apparatus. Additionally, the temperature sensor which is used to compensate for the effect of changes in ambient temperature on the calibration of the phase fluorimeter must also be tested. Additionally, in order to fully validate the sensor, the system should be tested at multiple values of phase delay in order to test it over the dynamic range of delays that the phase fluorimeter system will experience.

Figure 6:
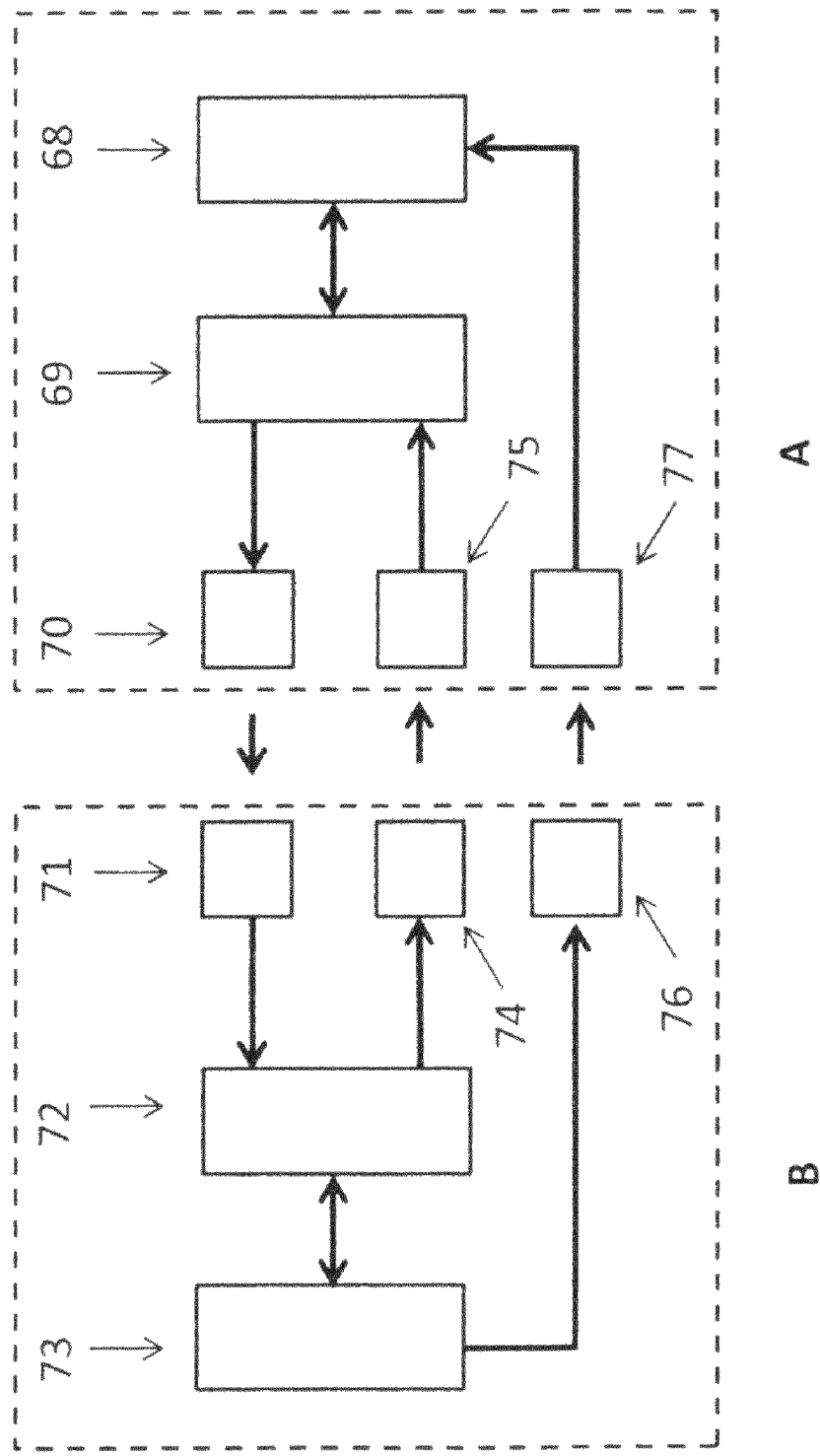
FIG. 6 is a block diagram of the system of the present invention.

A block diagram of the phase fluorimeter and the validation system of the present invention is shown in FIG. 6. In this Figure the phase fluorimeter being tested and the validation apparatus of the present invention are shown separately and labeled as A and B respectively. In the phase fluorimeter item 68 represents the overall processing electronics, 69 represents the signal processing electronics, i.e., the drive electronics for the light source and the detection electronics for the photodetector. When being tested, the light source 70 from the fluorimeter impinges upon the optical detector 71 in the validation apparatus and the signal from the optical detector is conditioned in the electronic signal processing system 72. The phase is delayed in the electronic signal processing system 72 to an amount set by the control system 73. The phase delayed signal is conditioned in the signal processing system 72 so that it can drive the light source 74. The light from 74 impinges upon the fluorimeter sensor's detector 75. The phase shift between the light produced by 70 and sensed by 75 is subsequently calculated in, and displayed by 68.

The control system 73 also controls a unit which actuates and measures temperature 76. Such a unit could be comprised of a thermo-electric cooler (TEC) and a temperature measurement device of sufficient accuracy. 76 will be in thermal contact with the fluorometric sensor's temperature measuring device 77. The junction of 76 and 77 will be suitably insulated from the thermal influence of the ambient environment. The temperature of 76 is measured by 77 and displayed in 68. The temperature sensor 77 is then tested (validated) by comparing the measured reading displayed The validation process needs to verify that the sensor provides phase measurements that are accurate and precise over the designed temperature range of measurement of the sensor. Therefore the temperature set by 73 and 76 should be measured through the entire extent of the temperature measurement range of the phase fluorimeter. The extent of this range will depend on the design of the phase fluorimeter.

Figure 7:
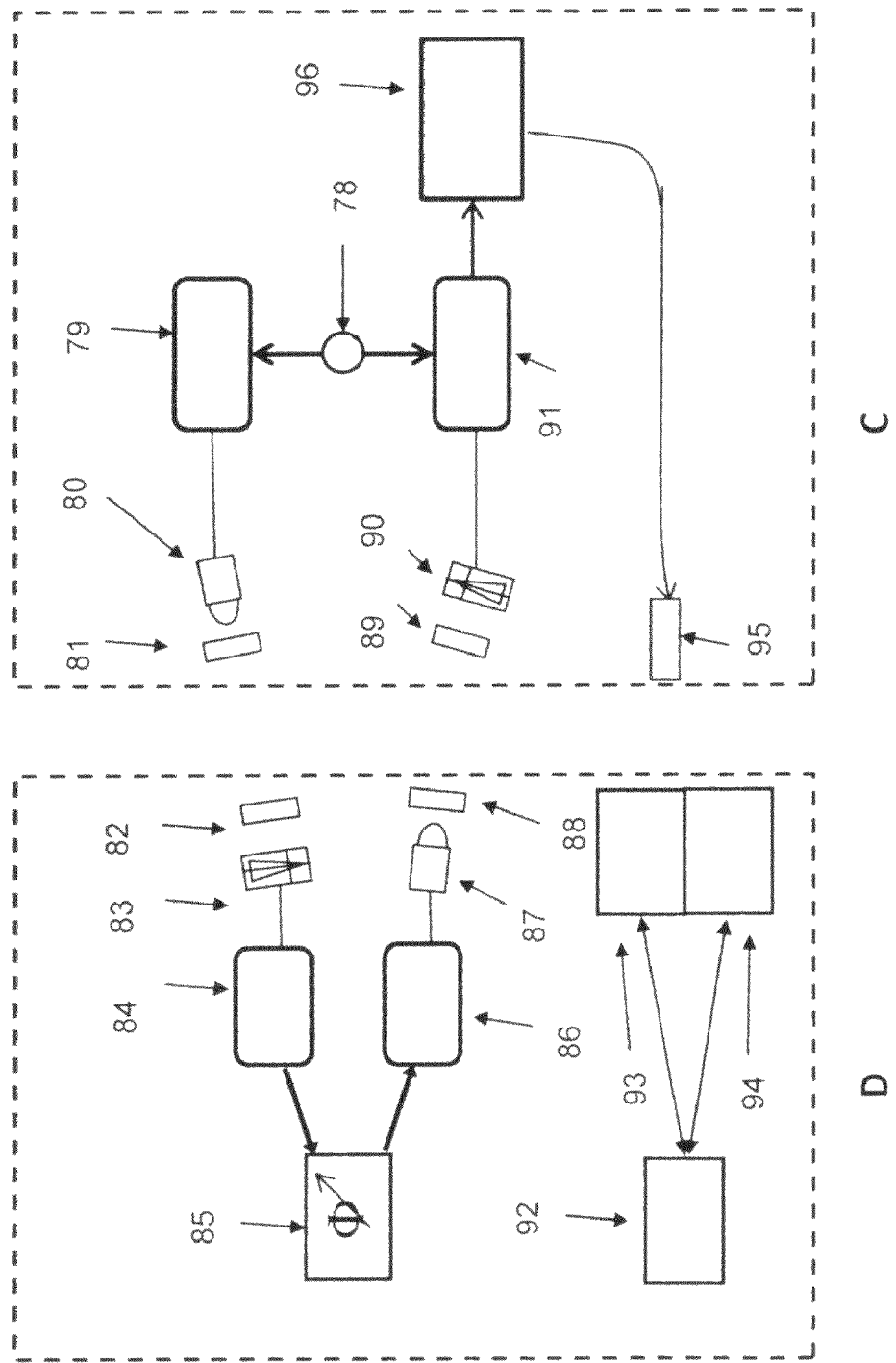
FIG. 7 is a schematic representation of an apparatus in accordance with the present invention for testing the response of a phase fluorimetric/electro-optic system.

An apparatus in accordance with the present invention for testing the response of a phase fluorimeter system is shown schematically in FIG. 7. FIG. 7 is divided between block C which is the phase fluorimeter and block D which is the apparatus of the present invention which is designed to validate (i.e., test the accuracy of) the phase fluorimeter. As shown, the excitation light from the phase fluorimeter impinges on a photo-detector 83 (e.g.: PIN, PN junction based photo-diode or equivalent device that converts an optical signal to an electrical signal) in the validation apparatus. This electrical signal can then be adjusted in its phase with respect to the excitation light phase in order to simulate different phase shifts. In the phase fluorimeter 78 is the sine generator which feeds electrical signal drive circuit 79. The electrical drive signal in turn drives optical device 80 (e.g., an LED, laser diode, etc). The optical signal traverses an absorptive or dielectric filter (or combined absorptive and dielectric or other suitable filter) 81 which tailors the light to match the absorption spectrum of the fluorophore which the fluorimeter is designed to utilize. When the phase fluorimeter is being validated by the apparatus of the present invention, the light emitted by the fluorimeter light source is directed to the validation apparatus which will preferably include a filter 82 as shown which allows only the light emitted by the phase fluorimeter (e.g., no ambient light) through to photo-detector 83. The electrical signal from photodetector 83 is amplified and the signal is processed by component 84. This signal is passed to 85 where a variable phase delay is imparted. The electrical signal is then conditioned by 86 to drive a light source (e.g., LED, laser diode, etc) 87. This phase delay simulates the presence of a fluorophore which is quenched by different analyte concentrations. Components 84, 85 and 86 will normally be combined in an integrated unit but are shown here as separate components for purposes of clarity. 84 is comprised of electronic components that condition the electrical signal from the photodetector and present it in an appropriate manner to a variable phase shift generator 85. In order to present an appropriately conditioned signal, 84, 85, and 86 could be variously comprised of one or more of amplifiers, filters, current to voltage converters, or analog to digital converters. 85 introduces a variable phase shift to the sinusoidal signal. 86 receives this signal and drives the light source. The result is that the light emitted by light source 87 is at a controlled phase shift relative to the excitation light from the phase fluorimeter optical device 80. The light from the validation apparatus light source 87 is preferably filtered by a filter 88 to allow appropriate throughput to the fluorimeter through its filter 89 and subsequent stimulation of the fluorimeter detector 90. The optical filter 88 is designed to pass light of a wavelength which will stimulate the detector of the fluorimeter and also ensure that no light from 87 impinges on detector 83. Many kinds of known dielectric or absorptive filters could advantageously be used in this application. The phase fluorimeter measures the phase delay introduced by the verification apparatus with respect to the phase of the sinusoidally modulated original excitation signal from 79 as a reference in the fluorimeter phase measuring electronics 78. This phase delay number is displayed and can be communicated to the user via suitable electronics 96. The validation (or not) arises by comparing the number measured and displayed by the fluorimeter C with the specific variable phase delay provided by apparatus D. If the numbers coincide then the fluorimeter is reading correctly.

As mentioned before, the operating temperature of the fluorophore is also important and must be both accurately and precisely measured by the phase fluorimeter. Therefore the validation apparatus of the present invention needs to also confirm the ability of the phase fluorimeter to accurately and precisely measure temperature. This can be accomplished by incorporating in the validation apparatus a suitable driver 92 which actuates and measures the temperature of a device such as a thermoelectric cooler (TEC) 93 attached to a temperature measuring device 94. This device will be in thermal contact with the fluorometric sensor's temperature measuring device 95 to thereby maintain the temperature of 95 at the same temperature as 93. This can be accomplished, for example, using indium foil, thermal paste or other materials which is interposed between components 95 and 93 to thereby enable thermal contact between the TEC and the fluorimeter. All of 93, 94 and 95 are preferably insulated from outside thermal influence by the ambient environment.

Figure 8:
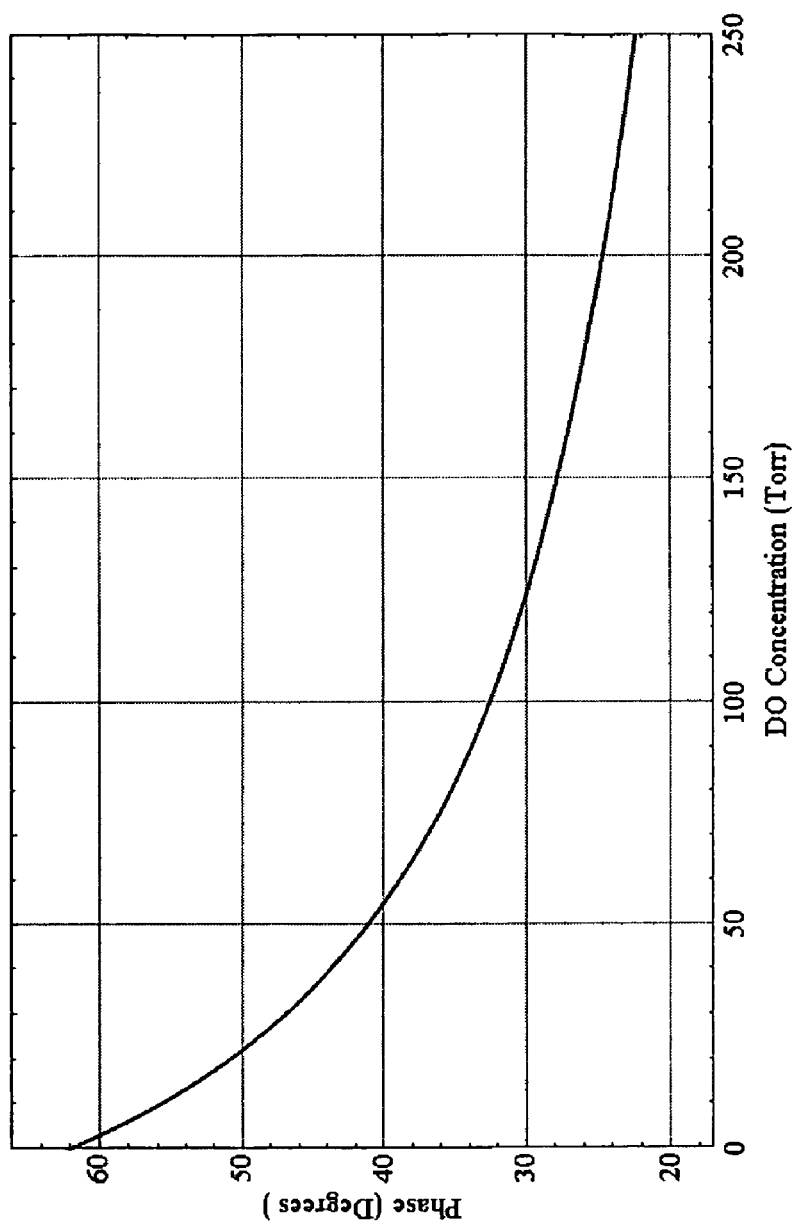
FIG. 8 shows an actual curve of phase delay vs. concentration of analyte (in this case oxygen).

For a given sensor dye (fluorophore) the typical response function is approximately known. This means that the range of phases expected is known. This determines the range of phases that the validation device tests the fluorimeter over. The phase delay delaying of synthesized light can be scanned in incremental values over the entire extent of expected phases to simulate those that would be seen in practice and validate the function of the phase fluorimeter C over its entire operating range. An actual curve of phase delay vs. concentration of analyte (in this case oxygen) is shown in FIG. 8. For this case, the phase would be tested at least over the range 22 degrees of phase shift to 64 degrees of phase shift.

We claimed

1. A validation apparatus for testing the measurement accuracy of a plurality of phase fluorimeter comprising:
   i) a photo-detector responsive to the excitation light emitted by a phase fluorimeter;
   ii) electronics connected to said validation apparatus photo-detector which calculates the phase of the light emitted by the phase fluorimeter and causes
   iii) a light source present in the validation apparatus to emit light of a wave length which will stimulate a detector of the phase fluorimeter but which is phase shifted relative to the excitation light emitted by the phase fluorimeter.

2. Apparatus in accordance with claim 1, further comprising optical elements for directing the light emitted by said validation apparatus light source through an optical filter which passes only light of a wave length which will stimulate the detector of a phase fluorimeter.

3. An apparatus in accordance with claim 1 further comprising:
   a thermal actuator suitable for being placed in thermal contact with a temperature measuring device of a phase fluorimeter.

4. An apparatus in accordance with claim 1 wherein said light source is an LED or diode laser.

5. An apparatus in accordance with claim 3 wherein said actuator is a thermo-electric cooler.

6. An apparatus in accordance with claim 3 wherein said thermal contact is achieved using indium foil.

7. A validation apparatus in accordance with claim 1 further comprising a second optical filter which passes to said validation apparatus photo detector only light emitted by a phase fluorimeter.

8. A process for testing the measurement accuracy of a phase fluorimeter comprising the steps of:
   i) passing to the photo detector of a validation apparatus in accordance with claim 1, light emitted by said phase fluorimeter,
   ii) calculating the phase of the light emitted by the phase fluorimeter and causing a light source present in said validation apparatus to emit light of a wave length which will stimulate a detector of the phase fluorimeter but which emitted light is phase shifted relative the light emitted by the phase fluorimeter;
   iii) directing the light emitted by said validation apparatus light detector of the phase fluorimeter and causing the fluorimeter to measure the phase source to the delay of the directed light relative to the light emitted by the phase fluorimeter; and iv) comparing the phase shift imparted in step ii) with the measured phase shift as reported by the fluorimeter in response to the light impinging on the detector of the phase fluorimeter.

9. A process in accordance with claim 8 comprising the additional step of setting and controlling the temperature of a thermal actuator present in said validation apparatus to test the temperature measurement components of the phase fluorimeter.

10. A process in accordance with claim 8 comprising the additional step of passing the light emitted by the phase fluorimeter through a filter of the validation apparatus which will pass to said validation apparatus photo detector only light of a wave length emitted by the phase fluorimeter.

\* \* \* \* \*